United States Patent [19]
Glomb

[11] 3,933,532
[45] Jan. 20, 1976

[54] METHOD FOR EXPOSING SURFACE DEFECTS ON HOT STEEL BLANKS

[75] Inventor: Klaus Glomb, Pumpchen, Germany

[73] Assignee: Eschweiler Bergwerks-Verein Aktiengesellschaft, Kohlscheid, Aachen, Germany

[22] Filed: Jan. 24, 1975

[21] Appl. No.: 543,671

Related U.S. Application Data

[63] Continuation-in-part of Ser. No. 393,712, Sept. 4, 1973, abandoned.

[30] Foreign Application Priority Data

Sept. 20, 1972 Germany.......................... 2246157

[52] U.S. Cl. .................. 148/6.35; 72/40; 134/19; 134/34
[51] Int. Cl.² ...................... C21D 1/82; C23F 7/04
[58] Field of Search ........... 148/6.35; 134/2, 34, 19, 134/37; 72/39, 40; 29/81 B

[56] References Cited
UNITED STATES PATENTS

| | | | |
|---|---|---|---|
| 1,898,809 | 2/1933 | Berg | 134/19 X |
| 2,282,397 | 5/1942 | Deck | 134/19 X |
| 2,394,514 | 2/1946 | Evans et al. | 134/15 X |

Primary Examiner—Ralph S. Kendall
Attorney, Agent, or Firm—Arthur B. Colvin

[57] ABSTRACT

The present method makes it possible to expose or make visible surface defects on or in the surface of steel blanks by heating the blanks to a temperature below the hot working temperature of the particular type of steel and thereafter rapidly descaling the blanks by means of high pressure water which contacts the steel for a limited time so as to avoid a substantial chilling or quenching. After such descaling the blanks are cooled at a controlled rate to thereby produce an oxidation film on the descaled surface which film makes the defects visible.

5 Claims, No Drawings

METHOD FOR EXPOSING SURFACE DEFECTS ON HOT STEEL BLANKS

The present invention is a continuation-in-part application of my copending application Ser. No. 393,712 filed Sept. 4, 1973, now abandoned.

BACKGROUND OF THE INVENTION

The present invention relates to a method for exposing surface defects on steel blanks having a given hot working temperature. The term "steel blanks" as used herein is intended to cover billets, slabs, ingots, rods, wire and the like. The surface defects are made visible by a particular type of descaling and controlled cooling as disclosed herein.

It is known to make surface defects in steel blanks visible by first permitting the blanks to cool down to room temperature and then descaling the surface of the blanks, for example, by shot or sand blasting or by grinding. In another known method the blanks are subjected to a pickling operation, whereby the pickling liquid has normally a temperature of about 60°C. Shot and sand blasting have the disadvantages that fine cracks and holes in the blank surface are closed by the impact of the shot pellets or the sand and thus become invisible. Pickling on the other hand changes the entire surface of the blank in such a manner that it becomes hard to discover small defects especially very narrow cracks and tiny holes. Besides, both methods, blasting and pickling, have the disadvantage that they may be performed only after the blanks have cooled down. Hence, it is not possible to take corrective steps in the manufacturing process, especially where a continuous manufacturing process is involved, such as extrusion casting or continuous casting. This is especially undesirable where the number of defects is high, because the descaling after the cooling may thus make it necessary that all blanks of an entire charge must be discarded, because of an accumulation of defects.

The rolling of coarse oxidation scale into the surface of the blanks is undesirable for several reasons, for example, such scale may later on damage any shaping tools which are employed in further machining the blanks. Such rolled in scale also reduces the quality of the product itself. Thus, it is well known to remove scale by means of water jets under high pressure prior to a hot working operation, such as drawing, piercing, or pressing. Reference is made in this connection to U.S. Pat. No. 2,394,514 granted on Feb. 5, 1946. Reference is made in this connection further to U.S. Pat. No. 1,898,809 granted on Feb. 21, 1933 where it is said that the application of water as an intermediate cleaning step will not interfere with the prompt reforming or reshaping of the heated and cleaned metal objects. However, since immediately after the hot working such as die shaping or pressing the oxidation continues to form new scale, the surface defects will not remain visible for an inspection subsequent to the hot working. Thus, contrary to the assumptions as, for example, stated in U.S. Pat. No. 1,898,809 that a descaling subsequent to the hot working is not necessary, it has been found that very minute surface defects require a descaling and controlled cooling subsequent to the hot working of the blanks as disclosed herein, especially where it is intended to keep the defects visible for longer periods of time.

OBJECTS OF THE INVENTION

In view of the foregoing, it is the aim of the invention to achieve the following objects singly or in combination:

to overcome the above outlined drawbacks of the prior art;

to descale and cool the blanks after their hot working in such a manner that the formation of a thin oxidation layer enhances the visibility of surface defects even if they are of a minute nature, such as very narrow cracks and small holes;

to assure the visibility of surface defects while the blanks are still relatively hot and to maintain such visibility even after the blanks have cooled down to room temperature;

to provide a descaling and subsequent controlled cooling in such a manner that an oxidation film is formed which tenaciously adheres to the surface of the blank thereby simultaneously enhancing the visibility of the surface defects and preventing a further scale formation;

to make surface defects of hotworked blanks so clearly visible that the monitoring may be done by automatically operating defects indicator devices, which detect and display such defects; and to make the defects visible while the blanks are still well above the temperature at which defects have been made visible heretofore, and to maintain the visibility of such defects even down to room temperatures.

SUMMARY OF THE INVENTION

According to the invention there is provided a method for exposing surface defects on steel blanks having a given hot working temperature, comprising employing blanks heated to a temperature within the range of about 500° to about 1100°C, which temperature is below the given working temperature of the particular type of steel blank, which is then rapidly descaled by exposing the heated blanks to cold water under pressure within the range of about 100 atm to 500 atm gauge pressure, thereby limiting the exposing to a duration which is rather short, for example, a fraction of a microsecond to a few hundreths of a second, so that any substantial chilling or quenching of the blank is avoided. Thereafter the cooling of the descaled blank is controlled at a rate which will produce an oxidation film on the descaled surface, whereby the oxidation film makes the surface defects visible. The cooling rate may preferably be within the range of 10°C per minute to about 100°C per minute.

DETAILED DESCRIPTION OF AN EXAMPLE EMBODIMENT OF THE PRESENT METHOD

Before describing a specific example it will be clarified what is meant by "hot working temperature" in the present context. Such temperatures will generally fall into a temperature range which in turn depends primarily on the steel composition and which also depends on the type of the working operation. Such temperatures are well known to those skilled in the art and may, for example, be gathered from tables which correlate the deformation temperature, for example of a non-alloyed steel to the carbon content of the particular steel involved. In connection with alloyed steels, the best hot deformation or working temperature range will usually be determined by well known methods and depending upon the particular type of alloy. The determination of such hot working or deformation temperature ranges is not part of the present invention.

According to the invention a steel blank, preferably one which has previously been hot worked is heated or has a temperature within the range of about 500° to 1100°C and such temperature is kept below the given hot working temperature of the particular steel blank. Thereafter, a rapid descaling is accomplished by exposing the heated blank to cold water jets under pressure within the range of about 100 atm to 500 atm gauge pressure. The exposure time or duration is limited to about 1/10,000th of a second to about 3/100ths of a second so that any substantial chilling or quenching of the blank is prevented. Thereafter controlled cooling is employed so that the cooling rate of the descaled blank is maintained within a temperature gradient range of about 10°C per minute to about 100°C per minute to produce an oxidation film on the descaled surface which makes the surface defects visible while the blank is still at relatively high temperatures. The advantage of this film is especially seen in that it maintains the visibility even down to room temperatures, in other words it prevents the new formation of scale on the surface of the hot worked blank.

In order to prevent a substantial chilling or quenching by the descaling it is preferable to make sure that the temperature drop does not exceed about 20°C.

The controlled cooling results in said oxitation film, which has a thickness of about $1\mu$ and sticks uniformly to the entire descaled surface of the blank.

In practice the descaling may, for instance, be accomplished by moving the hot worked blanks through a descaling zone past water jets at a speed of about 22.5 meters per minute, whereby the width of the individual jets is limited to about 5 to 10 mm, thereby assuring a contact time of about 1.33 to about $2.67 \cdot 10^{-2}$/second. Where the diameters of the hot worked blank are small, for example, in the formation of steel wire, the travelling speed through the descaling zone, may for instance, be 50 meters per second thereby assuring contact times of about 1 to 2/10,000ths of a second ($10^{-4}$). If desired the descaling zones may hold several spray rings arranged in series.

It has been found that the best temperature to be reached at which the descaling should be employed for non-alloyed steels is about 600°C. If desired, a rapid cooling prior to the descaling and subsequent to the hot working may be employed at a cooling rate of about 10° to 15°C per minute.

Although the invention has been described with reference to specific example embodiments, it is to be understood, that it is intended to cover all modifications and equivalents within the scope of the appended claims.

What is claimed is:

1. A method for exposing surface defects on steel blanks having a given hot working temperature, comprising the following steps:
    a. employing blanks heated to a temperature within the range of about 500° to 1100°C whereby such temperature is kept below said given hot working temperature of the particular steel blank,
    b. rapidly descaling the heated blank by exposing the heated blank to cold water under pressure within the range of about 100 atm to 500 atm (gauge) thereby limiting the exposing to a duration of about $1.10^{-4}$ seconds to $3.10^{-2}$ seconds so that any substantial chilling of the blank is avoided, and
    c. controlling the cooling of the thus descaled blank with a cooling rate within the range of about 10°C/minute to about 100°C/minute, to thereby produce an oxidation film on the descaled surface which oxidation film makes said surface defects visible.

2. The method according to claim 1, further comprising limiting the temperature loss due to said rapid descaling to about 20°C whereby any substantial chilling is avoided.

3. The method according to claim 1, wherein said oxidation film produced by said cooling has a thickness of about $1\mu$.

4. The method according to claim 1, wherein said oxidation film sticks uniformly to the descaled surface of the blank.

5. The method according to claim 1, wherein said rapid descaling and controlled cooling is performed on blanks which have been worked at a temperature above said given hot working temperature and the temperature of which has dropped below said given hot working temperature.

* * * * *